United States Patent [19]  [11] 3,988,438
Weinstein  [45] Oct. 26, 1976

[54] HAIR CONDITIONING SHAMPOO
[75] Inventor: Morris Weinstein, Paramus, N.J.
[73] Assignee: American Cyanamid Company, Stamford, Conn.
[22] Filed: Jan. 10, 1975
[21] Appl. No.: 540,353

[52] U.S. Cl. .............................. 424/70; 252/DIG. 2; 252/DIG. 3; 252/DIG. 13; 252/117; 424/DIG. 2; 424/359; 424/361
[51] Int. Cl.² ........................................ A61K 7/06
[58] Field of Search ................ 424/DIG. 2, 70, 361, 424/359; 252/117, DIG. 2, DIG. 3, DIG. 13

[56] References Cited
UNITED STATES PATENTS
2,426,125  8/1947  Steiner ............................. 260/209.6
3,149,338  9/1964  Habicht et al. ....................... 424/70
3,808,329  4/1974  Bolich et al. .......................... 424/70

OTHER PUBLICATIONS
Schimmel Briefs, No. 358, 2 pp., Schimmel & Co., Inc., New York, Jan. 1965.
Balsam et al., Cosmetics, Science and Technology, 2nd ed., vol. 2, Wiley–Interscience, New York, pp. 76–77 and 87–88, (1972).

Primary Examiner—James O. Thomas, Jr.
Assistant Examiner—Vera C. Clarke
Attorney, Agent, or Firm—Charles J. Fickey

[57] ABSTRACT
Hair shampoo composition which provides both cleansing properties and conditioning properties which makes it unnecessary to use a separate cream rinse. The composition is a combination of natural soaps, a syndet and an alginate salt.

1 Claim, No Drawings

HAIR CONDITIONING SHAMPOO

BACKGROUND OF THE INVENTION

This invention relates to improved aqueous shampoo compositions and more particularly to aqueous shampoo compositions with properties which both cleanse the hair and scalp, and in addition impart effects to the hair so that further subsequent treatment with rinses to overcome objectional effects is not necessary.

In practice to achieve satisfactory results it is customary to use a shampoo for the cleansing effect on the hair and scalp and then to apply subsequently a rinse to the wet cleansed hair to leave the hair in a pleasing and satisfactory, soft, lustrous and easily manageable condition.

An object of this invention is to provide a one-step combination hair shampoo and rinse conditioning composition so that desirable effects are obtained simply by applying the shampoo composition by conventional means with a subsequent customary creme rinse step being unnecessary.

Shampoos generally are aqueous compositions with cleansing agents and with other components or additives present for the purpose of improving performance with respect to the cleansing action on the hair and scalp and insofar as possible, to leave the hair in the desired, pleasing and satisfactory condition.

An important feature of any shampoo composition including creme rinse operations is the achievement of a condition of the wet hair after the shampoo operation which avoids a tangled condition and allows ease of combing without pulling, tugging or further entangling of the hair. This is particularly true in the "long hair" styles prevalent in today's youth oriented culture. Thus, the hair in present day styles, because of the greater length, tangles more easily and the entanglement produced is more difficult to comb out. It is desirable to have a shampoo composition which, in addition to producing a normally good flash foam with a good cleansing action and easy rinseability, will produce a condition in both long and short hair which promotes an improved wet combability where the comb drag is reduced and where the hair when dried has a desirable body, softness and luster.

There have been many attempts in the past to improve the conditioning effects of shampoos including wet combability by the addition of various conditioning agents, for example by the inclusion of an agent such as lanolin. However, in practice, to obtain the best results generally, a separate creme rinse operation is necessary. It often happens that the conditioning agents used in the creme rinse formulations cannot be effectively included in the shampoo composition for a variety of reasons, including incompatibility and loss of effectiveness.

Various attempts to include other materials for improving conditioning effects have been made and there are a number of disclosures in the art on such attempts to obtain a satisfactory so-called "one-step conditioning shampoo" composition. Some degree of success has resulted, however, in many instances the results leave much to be desired.

The present invention is based on formulations containing an alginate salt in addition to the various cleansing agents and other conventional additives such as solvents, stabilizers, preservatives, sequestrants, perfume and colorants.

Although improved results are obtained using an alginate salt in the presence of various types of cleansing agents such as anionic, nonionic, amphoteric, etc., the combination of the alginate salt in the shampoo composition, with certain cleansing agents as described below provides preferred types of compositions, such compositions affording a very definite improvement.

The alginate salt which may be used in the shampoo composition in the invention is preferably the triethanolamine salt (TEA) although other amine salts may also be used. The TEA salt however is preferred. This may be added to the composition as such or may be prepared in situ by adding the TEA and the alginic acid separately.

The cleansing agents used in the shampoo compositions may be conventional detergent types normally used in shampoo compositions. However, a combination of cleansing agents of natural derivation is preferred. This is the combination of a TEA salt of a long chain fatty acid, preferably from 12 to 16 carbon atoms, as may occur naturally in coconut oil and the TEA salt of oleic acid (18 carbon atoms with unsaturation).

The compositions of the invention, contain in addition to the alginate salt, the combination of the TEA salts of these two long chain fatty acids, that is, the oleate and the $C_{12}$ and $C_{16}$ acid such as the laurate.

In addition to these two soaps, at least one other detergent is present which may be a so called synthetic detergent type syndet (such as sodium lauryl ether sulfate, sodium lauryl sulfate, coconut diethanolamide, etc.), or preferably a naturally derived detergent such as the TEA salt of the condensation product of a long chain fatty acid (coconut oil acid) chloride with a hydrolysate of a naturally occurring protein.

The shampoo compositions containing the alginate salt and wherein the cleansing agent soap content consists essentially of a two component soap, the TEA salts of lauric and oleic acids along with the protein derived fraction as defined above afford highly desirable shampoo compositions resulting in a simple, safe and pleasing lathering cleansing agent, leaving the hair in a soft, clean, non-tangled, lustrous, and easily manageable condition, an effect which is often achieved only by the use of numerous complicated additives which may have desirable effects; or which may be achieved only through the use of a separate step creme rinse application operation.

Of course, as stated, although the cleansing agent fraction made up of the above defined compounds performs the primary function of cleansing the hair, other conventional shampoo components for various purposes may be present in the shampoo formulation as are generally used in the art. These include, for example, solvents such as glycol type solvents, thickeners, such as methylcellulose compositions; and various preservatives, stabilizers, sequestrants, colorant, perfume, etc.; and other minor amounts of conditioning agents such as ethylene glycol monostearate.

It is known that soaps, including fatty acid TEA soaps, and protein hydrolysate detergents or other detergents used in the compositions containing the alginates have been at times used separately in shampoo formulations. The TEA fatty acid soaps have previously been suggested for use in certain shampoo formulations. Also protein hydrolysate derived detergents are also suggested as components in shampoos. However, the use of a combination of the naturally derived TEA fatty acid soaps mentioned above (not a fatty alkyl sulfate salt detergent) and a naturally derived protein detergent along with the alginate salt, offers a shampoo composition which gives a maximum desirable effect minimizing the necessity for use of a creme rinse conditioning composition after the shampoo operation itself has been completed and such a composition is preferred.

The TEA fatty acid soap suitable for the shampoo composition includes the soap from long chain acids of from 12 to 18 carbon atoms as occur naturally (as esters or glycerides, for example, in coconut oil). These include lauric (12 carbons), myristic (14 carbons), palmitic (16 carbons) and oleic (18 carbons) acids. Preferred soaps are the TEA salts of lauric acid and oleic acid. The soap may be added as such to the other components of the composition or it may be formed in situ by the addition separately of TEA and the long chain acid to the formulation mix.

The protein derived detergent is the result of the hydrolysis product of a protein (such as collagen protein) reacted with or condensed with a long chain acid chloride, the condensed product then being neutralized with TEA. A particularly suitable protein derived cleansing agent is the TEA salt of the condensation product of naturally occurring coconut fatty acids with the hydrolysis product of collagen protein. A suitable product is one available commercially and identified as Maypon 4CT detergent. Related protein derived cleansing agents are also suitable for the shampoo composition where the condensation product is neutralized with potassium or sodium hydroxide; these commercially available products being identified also as Maypon, 4C and XK, for example.

The protein derived cleansing agents or detergents such as the TEA salts as mentioned above having protein derived hydrolysis and condensation products are also defined and described, for example, in "Soap and Chemical Specialities", Vol. 39, p. 82 (1963) and in "Specialities", Vol. I (11) p. 15, (1965). Such products identified commercially as members of the Maypon family admittedly have been used in previous shampoo formulations.

In the aqueous shampoo compositions of the invention, certain organic solvents or solvating agents may be used in addition to water, including for example, a glycol such as propylene glycol, sorbitol, glyercine, etc.; in addition to minor amounts of various other additives as mentioned above.

In the shampoo compositions of the invention, the alginate salt may be present to the extent of about 0.5 percent to 10 percent based on the total composition, but preferably in the range of about 2 to 4 percent. In some instances, the shampoo composition will be formulated in a concentrated form for subsequent dilution with water depending on the water content in the concentrated form. A corresponding adjustment of the concentration of the alginate salt would naturally have to be made.

The detergent or cleansing agent components of the shampoo compositions may be of natural derivation or synthetic derivation or a combination of the two. The preferred cleansing agent fraction as stated above is a combination of two naturally derived cleansing agent more specifically described as an amine soaps, preferably triethanolamine salts of a long chain fatty acid of 12 to 16 carbon atoms and oleic acid; and a naturally derived "protein detergent" type preferably as stated above, the TEA salt of the condensation product of a fatty acid chloride with a protein hydrolysate. The preferred composition has the combination of these preferred cleansing agents although other detergents, including synthetic detergents, may be present. In the preferred compositions, the combination of the TEA soaps and the protein derived detergent may be present at a concentration from 1t to 70 percent, and preferably in the range of 30 to 50 percent. The ratio of the TEA soaps to the TEA salt of the protein type detergent may be in the range of 1:2 to 2:1 in the improved alginate shampoo formulations. The TEA oleate is normally present in a concentration of about 8 to 12 percent on the total composition.

The shampoos are applied by conventional means. In evaluating the shampoos, a number of observations are normally made, including in the wet evaluation observation on the flash lather, the volume of lather, the feeling of the lather as to whether it has a creamy and pleasant feeling and the measure of how long the lather lasts. Further, the ease of rinseability is observed in addition to the look and feel of the hair as to cleanliness when it is wet, detangling effect, and the ease of wet combability. A dry evaluation is also made which involves observations as to texture, body, shininess of the hair, ease of brushing, lack of static, and whether there appears to be a residue left on the hair. Curl retention and manageability along with irritation to the scalp, ears, neck and eyes, are also significant. By comparison with the results of shampoo formulations containing no alginate or with comparative commercial shampoo formulations, the new compositions containing the alginates show a definite improvement. The presence of the alginates tends to promote a more stable creamier feeling lather. The wet feel of the hair and the handling feel in combing is improved with lack of tangling and with a feel of a velvety nature; and then after drying the dry hair has an improved body and sheen, can be more easily managed and more easily teased.

Although the invention is not intended to be limited in any way to the observation as to the mechanism whereby the improvement results, there may possibly be deposited on the hair a thin coating consisting of a plasticized TEA alginate film resulting in a pleasant feel with improved body and other superior results.

The invention is further illustrated by the Examples which follow.

In the Examples, shampoo compositions were prepared of the listed components.

EXAMPLE 1

| | Parts (%) |
|---|---|
| Lauric Acid | 10 |
| Triethanolamine (85%) | 5 |
| Triethanolamine oleate | 10 |
| Triethanolamine salt of coconut fatty acid chloride condensation product of collagen protein hydrolysate(1) | 15 |
| Glycerine | 10 |
| Triethanolamine | 9 |
| Alginic Acid | 3 |
| Sequestrant(2) | 1 |
| Preservatives(3) | 1.5 |
| Fragrance | as needed |

-continued

| | Parts (%) |
|---|---|
| Water | to make 100 |

(1) Maypon 4CT
(2) In this example and those following, a small amount of Versene (sodium salt of ethylenediaminetetraacetic acid) was used.
(3) In this example and those following, small amounts of preservatives or antibacterial were used, BHT (butylated hydroxytoluene) and Dowicil 200 (cis-isomer of 1-(3-chloroallyl)-3-5,7-triaza-1-azonia-adamantane chloride)

EXAMPLE 2

| | Parts (%) |
|---|---|
| Lauric Acid | 10.3 |
| Triethanolamine (85%) | 7.5 |
| Triethanolamine oleate | 10.0 |
| Triethanolamine salt of coconut fatty acid chloride condensation product of collagen protein hydrolysate | 15.0 |
| Glycerine | 10.0 |
| Sequestrant | 1.0 |
| Preservatives | as needed |
| Methocel(4) | 0.4 |
| Fragrance | as needed |
| Water | to make 100 |

(4) Small amount of thickener was used here to give a composition with viscosity to match that of composition of Example 1.

EXAMPLE 3

| | Parts (%) |
|---|---|
| Lauric Acid | 7.5 |
| Triethanolamine | 15.0 |
| Alginic Acid | 3.0 |
| Triethanolamine oleate | 7.5 |
| Triethanolamine salt of coconut fatty acid chloride condensation product of collagen protein hydrolysate(1) | 11.5 |
| Sorbitol (70%) | 10.0 |
| Sugar | 0.5 |
| Preservatives | 0.21 |
| Sequestrant | 2.0 |
| Fragrance | as needed |
| Water | to make 100 parts |

EXAMPLE 4

| | Parts (%) |
|---|---|
| Lauric Acid | 7.5 |
| Triethanolamine | 12.75 |
| Alginic Acid | 3.00 |
| Triethanolamine oleate | 7.5 |
| Triethanolamine salt of coconut fatty acid chloride condensation product of collagen protein hydrolysate | 11.5 |
| Glycerine | 10.0 |
| Sequestrant | 1.00 |
| Preservatives | 0.15 |
| Fragrance | as desired |
| Water | to make 100 parts |

EXAMPLE 5

For evaluation of the shampoo formulations, they were comparison tested by actual application to the hair on the heads of human subjects by experienced beauty operators. The hair of the subjects' heads were manually separated into two parts by the beautician prior to the application; two different shampoo compositions were applied to each subject, each composition being applied separately but in the same operation to each one-half of the head.

Observations are made to give a wet and dry hair comparative evaluation with respect to certain features of the shampoo operation comparing the results on each side of the head.

In the information which follows, results are described of the comparison of shampoo compositions of the invention with prior art compositions and with other commercial competitive products.

A. Comparison of Compositions of Example 2, no alginate, with Example 1, alginate containing composition of the invention The majority preferred the alginate composition and considered the results superior with respect to lather, lather volume, wet combability and cleanliness feel. As to the dry evaluation, the majority considered the alginate composition equal to or better than the non-alginate composition with respect to feel, luster, easy brushability, manageability, etc.

B. Comparison of Composition of Example 3 with a Commercially Available Shampoo Product Using 10 subjects with professional operators, there was a preference by the majority for the composition of Example 3 with respect to improved lather and creamy feel, improved wet combability effect and cleaner feel or appearance as to observations on the wet hair.

There was a majority report on the dry hair effects as to equal or improved clean feel and ease of brushing, improved body, texture and manageability.

C. Comparison of the Composition of Example 3 with Another Commercial Shampoo Composition Using 12 subjects there was a definite preference by the majority for the composition of Example 3 with respect to the flash lather, volume of lather and creamy feel of the lather. On observations on the wet hair, for the majority of subjects, the results were considered equal to or better with respect to clean feel of the hair, rinseability of the lather and wet combability. In the evaluation of the dry hair, there was a definite preference by the majority for the composition of Example 3 with respect to cleanliness of the hair, ease of brushing, texture, etc.

D. Comparison of the Composition of Example 4 with Still Another Shampoo Product Using 11 subjects with experienced operators, there was a definite preference for the composition of Example 4 on the wet hair observation for clean appearance and feel and ease of wet combability. On the dry evaluation there was a majority preference with respect to clean feel of the hair, improved body, ease of brushing, texture, and manageability.

What is claimed:

1. A hair conditioning shampoo composition which comprises water, from 0.5 parts to 5.0 parts of the triethanolamine salt of alginic acid and an effective amount of a cleansing fraction comprising the triethanolamine salts of long chain fatty acids of 12 to 16 carbon atoms and a $C_{18}$ unsaturated carbon acid in combination with the triethanolamine salts of the condensation products of a fatty acid chloride of 12 to 16 carbon atoms with a protein hydrolysate.

* * * * *